United States Patent [19]

Arnone et al.

[11] Patent Number: 4,642,107
[45] Date of Patent: Feb. 10, 1987

[54] ADAPTER FOR USE WITH TWO PIECE OSTOMY SYSTEM

[75] Inventors: Ronald Arnone, Naperville, Ill.; Keith Ferguson, Scotch Plains, N.J.

[73] Assignee: E. R. Squibb & Sons, Inc., Princeton, N.J.

[21] Appl. No.: 541,859

[22] Filed: Oct. 14, 1983

[51] Int. Cl.⁴ .............................................. A61F 5/44
[52] U.S. Cl. ................................................... 604/342
[58] Field of Search .............. 285/237, 225, 226, 423; 604/332–345; 607/277

[56] References Cited

U.S. PATENT DOCUMENTS 3,123,074  3/1964  Turner ................................. 604/332
4,419,100  12/1983  Alexander ........................... 604/341

FOREIGN PATENT DOCUMENTS 1105558  4/1961  Fed. Rep. of Germany ...... 604/338
1571657  7/1980  United Kingdom .
1586823  3/1981  United Kingdom .
1586824  3/1981  United Kingdom .
2115288  9/1983  United Kingdom .

Primary Examiner—C. Fred Rosenbaum
Assistant Examiner—J. L. Kruter
Attorney, Agent, or Firm—Lawrence S. Levinson; Stephen B. Davis

[57] ABSTRACT

An adapter comprising a channel shaped coupling member and a rib shaped coupling member connected by a continuous wall. The adapter coupling members are sized so as to fit between the body side and pouch of a two piece ostomy system.

2 Claims, 3 Drawing Figures

ADAPTER FOR USE WITH TWO PIECE OSTOMY SYSTEM

BACKGROUND OF THE INVENTION

Major abdominal surgery for a number of diseases involving different parts of the gastro-intestinal and urinary tract can result in a patient being left with an abdominal stoma. The three most common types of abdominal stoma are the colostomy, the ileostomy, and the ileal conduit. In the case of an ileostomy, ileal conduit, and many colostomy operations, the patient is unable to control the passage of bodily waste material and must rely upon an appliance attached to their body to collect this material.

Numerous appliances have been proposed for this purpose. Most can be characterized as either a one-piece or a two-piece system. The one-piece appliance conventionally consists of a pouch having an opening in one sidewall for the stoma around which a plastic faceplate is permanently bonded. The faceplate includes an outer layer of adhesive material which is designed to affix the appliance directly to the body or to an intermediate skin barrier or sealing washer. The two-piece appliance conventionally consists of a mounting ring that is supported on the body by means of an elastic belt.

Recently, the two-piece appliance disclosed by Steer et al. in British Patent Nos. 1,571,657, 1,586,823 and 1,586,824 has achieved considerable commercial success. The Steer et al. appliance consists of a skin barrier having a projecting rib type coupling member affixed to its outer surface and a pouch with a channel shaped coupling member encircling the stoma opening in the pouch sidewall. The pouch can be securely attached to the skin barrier by snapping onto the rib. The skin barrier employed by Steer et al. consists of a layer of pressure sensitive adhesive having an outer water insoluble polyethylene film to which the rib coupling member is affixed.

The act of assembling the two piece system of Steer et al. results in pressure being exerted against the body. This may be undesirable, particularly for the period of time immediately following surgery. Proposals for overcoming this difficulty have involved displacement of the rib coupling member from the surface of the skin barrier. This permits the fingers to be inserted beneath the rib so as to cushion the force exerted when the pouch is snapped onto the rib. Jensen in U.S. application Ser. No. 503,754 filed June 13, 1983 discloses such a system where the intermediate member includes a series of accordion-like folds.

SUMMARY OF THE INVENTION

This invention is directed to an adapter for use with a two piece ostomy system. In particular, the adapter is designed for use with a two piece ostomy system wherein the body side portion has an upstanding or projecting rib that serves as one coupling member and an ostomy pouch having a channel shaped coupling member.

The adapter consists of a channel shaped coupling member and a projecting rib coupling member joined together by a continuous relatively thin flexible polymeric wall. Preferably, the flexible polymeric wall includes one or more accordion folds. In use, the channel shaped coupling member of the adapter is sized to fit and snap over the rib coupling member of the body side portion of the two piece ostomy system. Similarly, the projecting rib coupling member of the adapter is sized to fit within the channel shaped coupling member of the ostomy pouch.

DETAILED DESCRIPTION OF THE INVENTION

Figure 1:
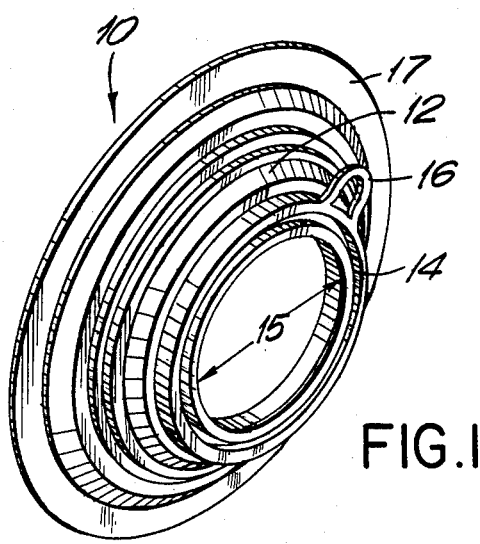
FIG. 1 is a perspective view of the adapter of this invention shown in its expanded state.
Figure 3:
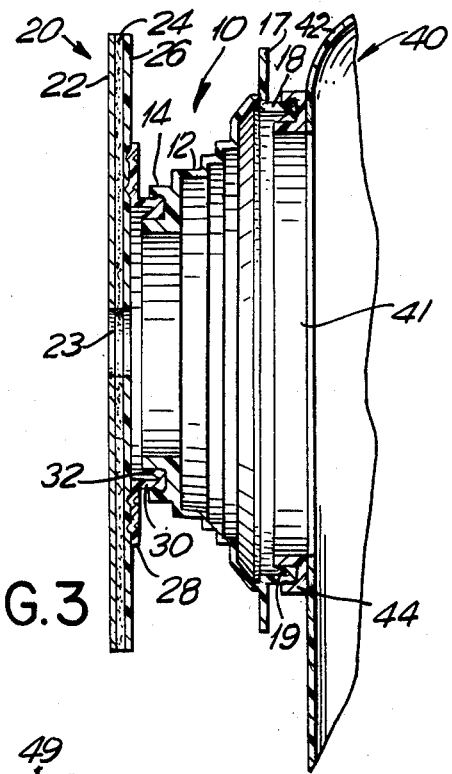
FIG. 3 is a sectional view showing the adapter of this invention in its expanded state assembled between a two piece ostomy appliance.

Adapter 10 as best shown in FIGS. 1 and 3 consists of a channel shaped coupling member 14 and a rib type coupling member 18 projecting perpendicularly from flange 17. Rib type coupling member 18 preferably includes a thin, resilient, deflectible seal strip 19 which extends inwardly from rib 18. The two adapter coupling members are connected by a continuous relatively flexible thin polymeric wall 12. Preferably connecting wall 12 is thermal formed so as to have one or more accordion-like folds. The channel shaped coupling member 14 can also include one or more pull tabs 16.

Adapter 10 is assembled by injection molding channel shaped coupling member 14 and projecting rib coupling member and flange 17, 18, 19. Preferably, these coupling elements are prepared from a low density polyethylene of about 30 mils thickness. Connecting wall 12 is thermal formed preferably from low density polyethylene of about 10 to about 15 mils thickness. Connecting wall 12 is then heat sealed to a circular flange 17 and channel coupling member 14.

Adapter 10 is employed in conjunction with the two piece ostomy appliance described by Steer et al. in the British Patents noted above. The body side portion 20 of this two piece system consists of a layer of pressure sensitive adhesive 24 having a thin film of polymeric material 26 attached to it. The other side of adhesive layer 24 is covered by silicone coated release paper 22 that is removed at the time of use. Body side 20 includes an aperture 23 which can be enlarged by the ostomate so as to fit snugly around the stoma. Flange 28 is attached to film material 26 and includes a rib type coupling member 30 projecting perpendicularly from flange 28. Rib type coupling member 30 preferably includes a thin, resilient, deflectible seal strip 32 which extends inwardly from rib 30.

Adhesive layer 24 is preferably a homogeneous blend one more water soluble or swellable hydrocolloids such as gelatin, pectin, guar gum, sodium carboxymethylcellulose, etc. dispersed in a viscous elastomeric binder such as polyisobutylene as described by Chen in U.S. Pat. No. 3,339,546. Optionally, the adhesive layer can also include one or more cohesive strengthening agents as described by Chen et al. in U.S. Pat. No. 4,192,785.

The ostomy pouch portion 40 of the two piece ostomy system consists of two bag walls 42 and 43 joined together along their peripheral edge 45. Bag wall 42 has an aperture 41 for passage of bodily waste from the stoma. The stomal aperture is encircled by a channel shaped coupling member 44 which is permanently affixed to bag wall 42 by heat sealing. Channel shaped coupling member 44 also includes a pull tab 46 and two ears 49 for the attachment of a belt if desired.

Pouch 40 is shown as having a bottom drain valve opening 48. Such a pouch is described in more detail by Steer et al. in U.S. Pat. No. 4,300,560. However, pouch 40 could also be of the disposable type in which case walls 42 and 43 are joined along their entire peripheral edge with no drain valve opening.

Figure 2:
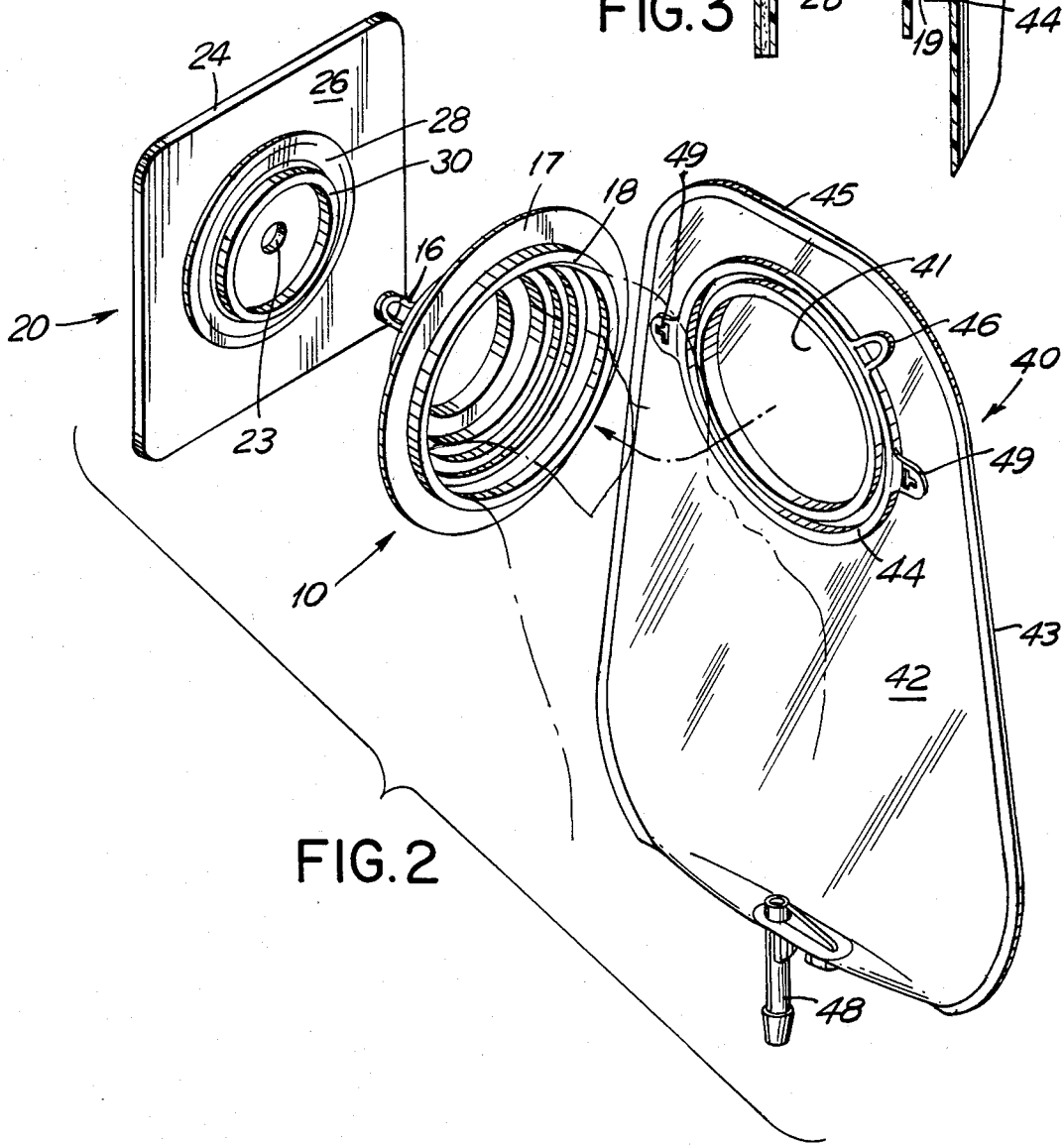
FIG. 2 is an exploded view showing the adapter of this invention as it fits between the body side portion and pouch portion of a two piece ostomy system.

In use, the aperture 23 of the body side portion 20 is enlarged to fit snugly around the stoma. The adapter 10 is attached to body side 20 by snapping channel coupling member 14 over coupling rib 30 so that deflectible seal strip 32 is deformed into a tight fit within channel 14. The silicone coated release paper is removed and the body side and attached adapter is affixed to the body. The adapter is lifted away from surface 26 so that the accordion folds are in an expanded state as shown in FIG. 3. Fingers are placed around the outside of the accordion fold as shown in FIG. 2 and the pouch 40 is affixed to the adapter 10 by snapping channel 44 over rib 18 so that deflectible seal strip 19 is deformed into a tight fit within channel 44.

As shown in the figures, aperture 15 of channel coupling member 14 is smaller than the aperture encircled by coupling rib 18. Thus, when accordion-like folds 12 are in their relaxed state, flange 17 will be near the polymeric film surface 26 of body side portion 20. This maintains a relatively flat profile for the assembled ostomy system.

If pouch 40 is of the disposable type, it is detached from adapter 10 by pulling tab 46. A new pouch can then be attached to adapter 10 by placing the fingers so that the accordion folds assume their extended state and snapping the new pouch in place. Similarly, a drainable pouch can be removed and later reattached to permit inspection of the stoma and cleaning or treating of the skin proximate to the stoma.

It is believed that the adapter of the present invention will be used primarily during hospital care. In the period of time following surgery, the patient is sensitive to the exertion of pressure against the body that can result from securely attaching a pouch. The adapter system of this invention has an advantage over the two piece accordion system of Jensen described in U.S. Ser. No. 503,754 in that the hospital or other health care facility does not need to inventory an entire stock of two different body side components. The hospital need only stock the conventional body side 20 to which the ostomate will be introduced prior to being discharged and one or two sizes of adapters. Also, the confidence of the patient will be increased since he will be using the same body side product throughout his hospital stay that he will be using in his daily life.

The deflectible seal strips 19 and 32 are shown in the figures as extending inward from the projecting rib which is preferred. However, the coupling system will also be effective if the seal strips extend outwardly. Also, in order to increase the security of the seal, the surface of the coupling ribs 18 and 30 opposite the deflectible seal strip can include a peripheral rim that cooperates with a rim in the channel shaped coupling element as taught by Steer et al. in British Patent No. 1,571,657.

What is claimed is:

1. An adapter that connects a two piece ostomy system which consists of a body side portion having an adhesive dressing to which a rib shaped coupling member is directly, permanently affixed and a collection pouch portion having a stomal aperture in one pouch side wall surrounded by a channel shaped coupling member permanently secured to said pouch side wall, said adapter having a longitudinal axis and proximal and distal ends extending longitudinally and consisting of a continuous, relatively thin, flexible polymeric annular wall having one or more accordion folds, a flange means extending perpendicularly to said longitudinal axis at the distal end of said polymeric adapter wall to provide support for a rib shaped coupling member, said flange including an upwardly projecting rib shaped adapter coupling member having an inwardly extending thin resilient deflect seal strip shaped to fit within the channel shaped coupling member of said pouch portion, and an adapter channel shaped coupling member secured to the other end of said polymeric wall, said adapter channel shaped coupling member sized to snap over the coupling rib affixed to said body side portion, and wherein the aperture encircled by said adapter channel shaped coupling member is smaller than the aperture encircled by said adapter rib shaped coupling member whereby when said accordion folds are in their relaxed state said adapter will have a low profile and in use will be near the surface of said body side piece.

2. An adapter as in claim 1 wherein said adapter channel shaped coupling member includes a pull tab.

* * * * *